United States Patent
Kubbies et al.

(10) Patent No.: US 6,251,672 B1
(45) Date of Patent: Jun. 26, 2001

(54) CULTURING MAMMALIAN CELLS IN CONTACT WITH CELL SURFACE PROTEINS

(75) Inventors: Manfred Kubbies, Penzberg; Peter Dörmer, Gilching; Petra Meissner, Jülich, all of (DE)

(73) Assignee: GSF-Forschungszentrum fur Umwelt und Gesundheit, Oberschleibheim (DE)

( * ) Notice: Subject to any disclaimer, the term of this patent is extended or adjusted under 35 U.S.C. 154(b) by 0 days.

(21) Appl. No.: 09/197,470

(22) Filed: Nov. 23, 1998

Related U.S. Application Data

(63) Continuation-in-part of application No. PCT/EP97/02475, filed on May 15, 1997.

(51) Int. Cl.[7] ............................. C12N 5/00; C12N 11/00; C12N 11/02; C12N 11/06; C12N 5/06
(52) U.S. Cl. ..................... 435/395; 435/174; 435/177; 435/180; 435/325; 435/347; 435/373
(58) Field of Search .................................. 435/174, 177, 435/180, 325, 347, 373, 395

(56) References Cited

FOREIGN PATENT DOCUMENTS

WO 94/23014    10/1994  (WO) .
WO 95/02040    12/1995  (WO) .

OTHER PUBLICATIONS

Loughrey HC et al., FEBS Letters 332, (1–2) 1993, pp. 183–188, "Characterisation of biotinylated liposomes for in vivo targeting applications".

Toksoz et al., Proc. Natl. Acad. Sci. (1992) 89 (16) pp. 7350–7354, "Support of human hematopoiesis in long–term bone marrow cultures by murine stromal calls selectively expressing the membrane . . . ".

Corley P. et al., Chemical Abstracts, vol. 121, No. 21, Nov. 21, 1994, abstract No. 245262, "Binding of biotinated–liposomes to streptavidin is influenced by liposome composition".

*Primary Examiner*—David M. Naff
(74) *Attorney, Agent, or Firm*—Arent Fox Kintner Plotkin & Kahn, PLLC

(57) ABSTRACT

Mammalian cells which require contact with cell surface proteins for activation, differentiation and/or proliferation are cultured in contact with an immobilized mammalian cell, with an immobilized membrane vesicle from a mammalian cell or with immobilized membrane vesicles from at least two mammalian cell populations. The mammalian cell or membrane vesicle can be modified with a first partner of a biological binding pair, and immobilized on a solid carrier via a second partner of the biological binding pair. Culturing can be with a first immobilized membrane vesicle and subsequently with a second immobilized membrane vesicle. The membrane vesicle contains part of the natural surface of a mammalian cell that includes a signal triggering surface protein. The membrane vesicle can be immobilized via a binding partner of a cell surface molecule.

19 Claims, 2 Drawing Sheets

CULTURING MAMMALIAN CELLS IN CONTACT WITH CELL SURFACE PROTEINS

CROSS REFERENCE TO RELATED APPLICATION

This application is a continuation-in-part of International Application PCT/EP97/02475, filed May 15, 1997, and designating the U.S.

BACKGROUND OF THE INVENTION

1. Field of the Invention

The invention concerns a process for culturing mammalian cells which require contact with cell surface proteins for activation, differentiation and/or proliferation as well as devices for culturing these cells.

2. Description of the Related Art

The culture of human cells is of major importance for various therapeutic approaches. Human cells cultured in vitro are for example required in adoptive immunotherapy with autologous or allogenic cells. Efficient processes for culturing haematopoietic progenitor and stem cells which for example can be transplanted into the patient after radiation therapy or chemotherapy are also of major importance.

Cytotoxic T lymphocytes (CTL) are responsible for eliminating pathogenically changed endogenous cells such as e.g. cells infected with viruses or tumour cells. In adoptive immunotherapy, lymphocytes of the patient are activated in vitro and then reimplanted. Such an activation can for example be carried out by adding interleukin 2 (IL2) to promiscuous killer cells (Thiele, D. et al., Immunology Today 10 (1989) 375–381). Such cells are then referred to as lymphokine-activated killer cells (LAK cells) (Rosenberg, Immunology Today 9 (1988) 58–62). However, LAK cells are also obtained in the stimulation with IL2 which are directed against healthy endogenous cells (Chen, B. et al., Cell Immunol. 118 (1989) 458–469). In a further method for adoptive immunotherapy, the lymphocytes to be activated are cultured in the presence of autologous tumour cells (Mixed Lymphocyte Tumor Cultures, Fossati, G. et al., International Journal of Cancer, 42 (1988) 239–245). A further method is described in WO 94/23014. According to this method lymphocytes are activated to form tumoricidal cells in a co-culture with a mammalian cell line while avoiding an allogenic stimulation. Fragments or vesicles of this cell line can also be used instead of the cell line described in this reference.

Suspended vital tumour cells or fragments thereof which have been previously advantageously inactivated by chemotherapy or radiotherapy are usually used for the ex vivo activation of CTLs. However, this process has major disadvantages. The inactivation of the tumour cells is complicated (irradiation, handling of toxic substances). It cannot be excluded that vital tumour cells or DNA from tumour cells are carried over into the transplant during transplantation.

Furthermore the inactivation of cells can lead to receptor modulations. Also the secretion of inhibitory molecules by for example inactivated tumour cells that are still alive cannot be excluded. Also the geometric/mechanical problem of the optimal cell density of effector to activator cells (probability of hits) is time-consuming and can only be determined empirically.

The immobilization of biological effectors on cell culture surfaces is used to activate cells and to proliferate them. Thus for example anti-T-cell antibodies are immobilized by preincubation on cell culture vessels by means of non-covalent binding. T cells that are added proliferate by binding/interaction of their CD3 receptors with immobilized (CD3) antibodies (Geppert, T. D., Lipsky, P. E., The Journal of Immunology 6, Vol. 138 (1987) 1660–1666).

Antigen-specific CTL's can be induced in a similar process by immobilizing MHC molecules alone (Walden, P., et al., Nature, Vol. 315 (1985) 327–329) or embedded in synthetic, planar membranes (Watts, T. H. et al., Proc. Natl. Acad. Sci. USA, Vol. 81 (1984) 7564–7568). Moreover the T cell activation can be modulated by interactions with immobilized accessory molecules (Moy, V. T., Brian, A. A., J. Exp. Med. 175 (1992) 1–7).

Furthermore cells can be immobilized by non-covalent binding on cell culture vessel surfaces. The binding of monocytes on FCS-coated culture vessels and pulsing with specific antigens leads, after co-culture with peripheral blood lymphocytes, to an improvement of the antigen presentation with increased antibody production of the B cells (Jahn, S., et al., Allerg. Immunol. 33 (1987) 239–244).

The preparation of artificial lipid vesicles is state of the art. These liposomes can, on the one hand, be loaded with proteins embedded in the lipid membrane to improve cell targeting in vitro (Herrmann, S. H., Mescher, M. F., Proc. Natl. Acad. Sci. USA, Vol. 78, No. 4 (1981) 2488–2492; Bloemen, P. G. M., et al., FEBS Letters 357 (1995) 140–144; Bergers, J. J., et al., Journal of Controlled Release 29 (1994) 317–327; Gregoriadis, G., Immunology Today, Vol. 11, No. 3 (1990) 89–97). On the other hand, chemotherapeutic agents can be enclosed in such vesicles to increase the local dose in order to induce cell death (Brown, P. M., Silvius, J. R., Biochimica et Biophysica Acta 1023 (1990) 341–351). The in vivo administration of artificial anti-tumour vesicles (liposomes) for antigen immunotherapy also corresponds to the state of the art (Phillips, N. C., et al., Liposomes in the Therapy of Infectious Diseases and Cancer, 1989, Alan R. Liss, Inc. (ed.), p. 15–24; Bergers, J. J., et al., Cancer Immunol. Immunother. 34 (1992) 233–240; Papahadjopoulos, D., Gabizon, A., Annals of the New York Academy of Sciences, Vol. 507, R. L. Juliane (ed.), 1987, 64–74).

In the previously known processes artificial liposomes/vesicles are either used in solution by non-covalent binding to carriers or in vivo. It is also known that cells labelled covalently via a binding partner can be used in a cell separation process to enable separation of bound specific cells from undesired cells by means of immobilized antibodies (EP-A 0 701 130).

A process for culturing haematopoietic progenitor stem cells using feeder layers of stroma cells is described in WO 95/02040. However, the preparation of such feeder layers is time-consuming.

SUMMARY OF THE INVENTION

The object of the invention is to provide an improved process for culturing mammalian cells which contact cell surface proteins of other cells during culture.

This object is achieved by a process for culturing a first mammalian cell which contacts cell surface proteins of a second mammalian cell for culturing characterized in that the said first mammalian cell is cultured in the presence of an immobilized vesicle of the second mammalian cell which contains parts of the natural surface of the second mammalian cell.

Instead of a vesicle of a second mammalian cell it is also possible to use a complete second mammalian cell. In this case a second mammalian cell is used which is modified with a first partner of a biological binding pair and is bound to a solid carrier via the second partner of the biological binding pair.

Figure 1:
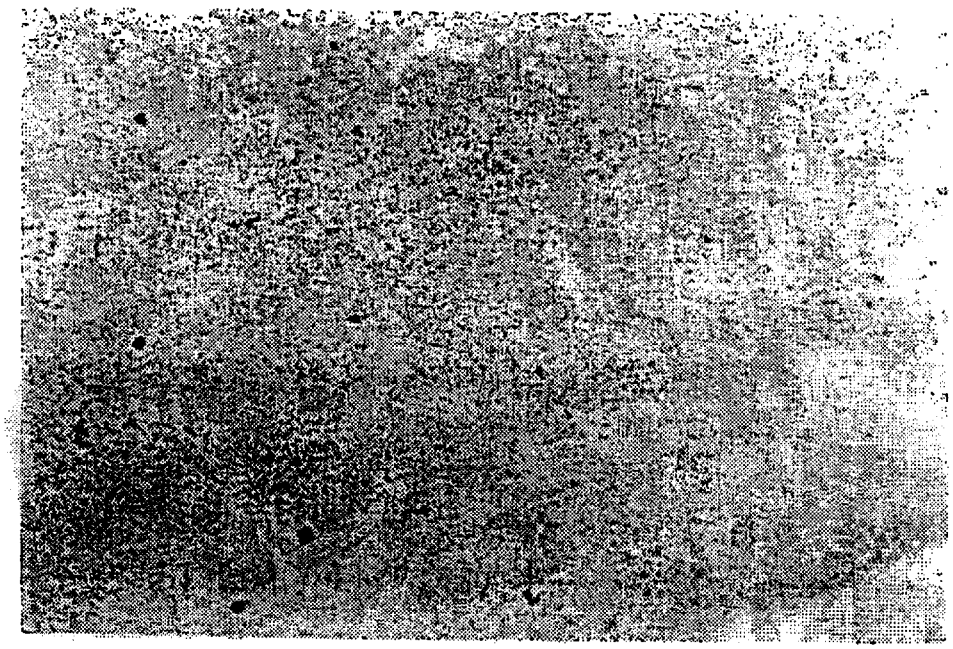
FIG. 1 shows the homogeneous coating of streptavidin-coated cell culture plates (96-well plates) with biotinylated vesicles of L88/5 bone marrow stroma cells (100× enlargement).

A–C: intact L88/5 bone marrow stroma cells

D–F: isolated vesicles of L88/5 bone marrow stroma cells.

A/D: morphological analysis of particles by forward and side scattered light (FSC vs. SSC)

B/F: Detection of cell-bound or vesicle-bound biotin on biotinylated L88/5 cells by means of FITC-labelled streptavidin (F11). Dead cells or vesicles of dead cells are labeled with propidium iodide (F12).

C/F: as B/F only on non-biotinylated L88/5 cells.

DETAILED DESCRIPTION OF THE INVENTION

It is expedient to immobilize the cells or membrane vesicles by incubation with a bindable carrier. The binding is achieved by means of a biological binding pair such as for example streptavidin/avidin, sugar/lectin, a CD molecule (e.g. CD3/anti-CD3 antibody), MHC molecules (class I or II) or digoxigenin/anti-digoxigenin antibodies.

The use of the binding partners streptavidin/biotin, avidin/biotin or derivatives of these compounds for the immobilization of cells or vesicles thereof has not been previously described. The preparation of biotinylated artificial liposomes in which biotin is bound to lipids was previously known (Bayer, E. A., Wilchek, M., Liposome technology, CRC Press Inc., 1984, Vol. III, 127–135; Loughrey, H. C., et al., FEBS 13102, Vol. 332, No. 1,2 (1993) 183–188). The characteristics of their binding to SA-labelled microtitre plates were examined and the primary aim was to bind these artificial biotin vesicles in vivo to SA-labelled cells (Corley, P., Loughrey, H. C., Biochimica et Biophysica Acta 1195 (1994) 149–156).

It has turned out that numerous simultaneously active interactions between cells, antigens and/or factors are necessary for the activation and differentiation of cells by other cellular binding partners (Herold, C., et al., MS-Medecine Sciences, Vol. 11, No. 5 (1995) 669–680; Clark, E. A. Ledbetter, J. A., Nature 367 (1994) 425–428; Mayordomo, J. I., et al., Nature Medicine, Vol. 1, No. 12 (1995) 1297–1302). Therefore the use of preferably biotinylated immobilized cells or native membrane vesicles derived therefrom is a major advantage since, surprisingly all necessary reaction partners are located on or in the membrane. Moreover such an artificial surface is a universal reaction system since partners that may be absent, e.g. in the case of mutated tumour cells, can be easily additionally applied by means of biological binding pairs.

Mammalian cells which are suitable for culture by the process according to the invention are cells which for their culture make a receptor and/or antigen contact with cell surface proteins of other mammalian cells. Hence bioequivalent cell surfaces are required for culture. Such surface proteins are for example MHC complexes, co-stimulatory signals or adhesion molecules (Mescher, M. F., Immunological Reviews 146 (1995) 177; Herold, C., et al., MS-Medecine Sciences, Vol. 11, No. 5 (1995) 669–680; June, C. H., et al., Immunology Today 15 (1994) 321).

The required complexity of the interactions of cell surface proteins for cell activation, cell differentiation and cell proliferation become particularly apparent when co-culturing bone marrow stroma cells with haematopoietic stem cells for the long-term culture of the latter cells (Sutherland, H. J. Eaves, C. J., Culture of Hematopoietic Cells, Freshney, R. J., et al., (eds.), Wiley Liss, N.Y., 1994, pp. 139; Koller, M. R., et al., Biotechnology 11 (1993) 358). This seems to also apply to the differentiation of T cells from haematopoietic precursor cells ex vivo where co-culture with foetal thymus cells/tissue is required (Dou, Y. M., et al., Thymus 23 (1994) 195).

The culture of the mammalian cell can according to the invention be an expansion, an enrichment of a particular sort of cell from a cell mixture, an activation, differentiation and/or a proliferation of a mammalian cell. The process can be applied particularly advantageously to the proliferation of cytotoxic T cells and the differentiation and proliferation of haematopoietic progenitor and stem cells in granulocytes, monocytes, erythrocytes, megakaryocytes and lymphocytes.

In a preferred embodiment the cultured cells are modified by genetic engineering during the culture for example by transfection with a vector or by transduction with a therapeutically relevant retrovirus (Einerhand, M. P. W., et al., Blood 81 (1993) 254; Nolta, J. A., et al., J. Clin. Invest. 90 (1992) 342). Such ex vivo genetically modified cells can be used for a gene therapy.

In addition to intact cells, vesicles or fragments of cells are also suitable for co-culture to which a binding partner of a biological binding pair is bound. Cells that are suitable as cells for preparing such fragments or vesicles are those which are usually used for the co-culture of mammalian cells. These are for example stroma cells as a feeder layer, thymus cells, antigen-presenting cells or other cells which carry the signals for a T cell activation. Such signals are essentially those which mediate cell contacts such as e.g. adhesion (for example via CD11a, CD18, CD54), antigen-specific recognition (by means of the MHC complex via T cell receptor) or co-stimulating signals (for example via B7/CD28). This can also include the presentation of growth factors (Toksoz, D., et al., Proc. Natl. Acad. Sci. USA 89 (1992) 7350).

Cell vesicles can be prepared by methods familiar to a person skilled in the art. Vesicles can for example be prepared by hypotonic shock or by incubation with cytochalasin B. Other methods are for example described in WO 94/23014. Vesicles are obtained by such production methods which present parts of the native cell surface of the starting cell to other cells but are themselves no longer capable of replication. Consequently such vesicles no longer contain a cell nucleus. The cell nuclei are preferably separated from the vesicles by filtration (ca. 2–5 μm pore diameter). If it is intended to use vesicles which are modified with a binding partner of a biological binding pair it is expedient to modify the intact cells and subsequently to form vesicles from these cells.

Binding of a binding partner of the biotin/streptavidin system or biotin/avidin system, preferably biotin, is carried out expediently by biotinylating the whole cells. In this process free amino groups of proteins located on the cell membrane are preferably bound to biotin. A suitable reagent for this is for example D-biotinoyl-y-aminocarboxylic acid-N-hydroxysuccinimide ester (biotin-7-NHS).

Whether and to what extent the cells or vesicles have to be further modified before immobilization (binding of a binding partner of the biological system to the surface) essentially depends on the binding pair that is used. If for example the binding pair CD3/anti-CD3 antibody or lectin/ sugar is used then it is not necessary to modify the cells or vesicles before immobilization. In this case it is sufficient if the carrier is for example coated with anti-CD3 antibody or lectin. The cells or vesicles can then bind via structures (CD3 or sugar) that are naturally present on their surface to the corresponding binding partner which is immobilized on the carrier. A further advantage of such a process is that defined vesicles can be selectively bound. For example vesicles can be prepared from a PBMNC preparation and only bind T cells (CD3+) via an anti-CD3 antibody. A similar differentiation of vesicles can also be accomplished with other suitable surface markers. In addition to a binding pair in which one binding partner occurs naturally on the surface of the cells or vesicles to be immobilized, it is also possible to use a binding pair where neither of the binding partners occurs naturally on the surface of cells or vesicles. In this case the cells or vesicles must be modified before immobilization. Preferably the partner of the biological system that is to be bound is bound covalently to the cell surface via an activated amino group. Such binding pairs are for example biotin/streptavidin, digoxigenin/anti-digoxigenin antibody. In this case it is preferable to use a binding pair whose affinity is very high.

In this process it is not necessary that vesicle and carrier each carry on their surface the respective opposite partner of the biological binding pair, but rather it is also possible that the vesicle and carrier carry the same binding partner on the surface. In this case the other binding partner must be added, preferably in soluble form for the immobilization. Thus for example the vesicle and carrier surface can be biotinylated and the immobilization is achieved by adding soluble streptavidin. It is also possible to bind CD3 protein to the surface of the carrier and to immobilize vesicles which carry CD3 protein on the surface by adding a soluble antibody which is directed against CD3.

In a further embodiment the vesicles can be modified with more than one binding partner. In this case they are bound to the carrier via a binding partner whereas other substances can be bound to the surface of the cells or vesicles by means of the other binding partner. Substances are preferably bound which are required for the activation, proliferation or differentiation of cell. Antigens are preferably used which can increase the immunogenicity of tumour cells (activation antigens such as B7, CD40, MHC II or ICAM).

However, it is also possible that the tumour cell vesicles lack essential signal-triggering surface proteins. Such surface proteins are normally either naturally present on the normal cells of tumour patients or are inducible. Such signal proteins are for example the co-stimulatory signal proteins of the B7 family or CD40, antigen-presenting receptors such as MHC I and/or MHC II, adhesion molecules such as ICAM-1 or LFA-3 which are usually provided by normal haematopoietic cells.

Therefore in a preferred embodiment of the invention a mixture of vesicles of different cell populations is used, preferably a mixture which contains tumour cell vesicles as well as other vesicles which carry co-stimulatory signal-triggering surface proteins. Such other vesicles are preferably prepared from haematopoietic cells, from monocytes, macrophages, dendritic cells or B cells. Such cells can quite generally be used to prepare other vesicles which naturally carry or provide the missing signals or induce the missing signals. In this process hybrid surfaces of mixed immobilized vesicles are for example formed from tumour cells and from normal cells. In this manner it is for example possible to induce effective CTLs in the co-culture of for example autologous T cells of tumour patients.

The cells which are selected to be used for the preparation of vesicles with signal peptides can be directly isolated or purified from body fluids or tissue such as blood and/or bone marrow. They can also be grown in vitro by suitable culture conditions. When mixed hybrid vesicle surfaces are prepared, the same amounts of the respective vesicles are preferably immobilized. Depending on the vesicle size and density of the vesicles to be immobilized it is, however, also possible to immobilize relative proportions which differ from this.

In a further embodiment the mammalian cells that are to be cultured are firstly contacted in a first step with a first sort of vesicles and, in a further culture step, are contacted with a further sort of vesicles. This is advantageously carried out until an adequate stimulation is achieved.

The vesicles preferably have a size of about 10–30% of the first mammalian cell to be cultured. If it is intended to co-culture with vesicles from different cells, these vesicles preferably have a size which enables a simultaneous contact with at least two different vesicles. With a cell size of ca. 10 $\mu$m, the vesicles are preferably below 4 $\mu$m preferably below 500 nm in diameter.

In a further embodiment such activating substances can also be bound to the surface of cells or vesicles if these are only modified with a binding partner. In this case the cells or vesicles are immobilized on the carrier via the binding partner in a first step and in a second step the activating substances are bound to the binding partners that are still freely available on the surface of the cells or vesicles. In the case of biotin as the binding partner, the cell or the vesicle is consequently firstly bound to the carrier via biotin/streptavidin interaction and subsequently streptavidin-bound B7 is added to the biotins that are still free on the surface of the cells or vesicles, or biotinylated B7 and soluble streptavidin is added.

Antibodies to MHC class I or MHC class II molecules can for example also be used as binding partners for cell surface receptors (if unmodified vesicles are used). Binding partners preferably on carriers coated with streptavidin or avidin. Such an incubation for immobilization can be carried out in a simple manner for several hours at room temperature or at an elevated temperature. Subsequently the non-immobilized fraction of the cells or vesicles is removed by washing.

In a preferred embodiment tumour cells, vesicles of tumour cells or lymphocytes isolated by means of a Ficoll gradient are used as second mammalian cells for co-culturing.

An advantage of the process according to the invention is that defined vesicles can be used for example in stromal two step cultures since they can be combined with different cytokines or ECM proteins and hence the culture conditions can be varied as desired. This results in a culture preparation that can be more readily controlled.

Therefore, in a preferred embodiment, growth factors such as, e.g. SCF, IL-1, IL-2, IL-3, IL-4, IL-6. IL-11, EPO, G-CSF,GM-CSF TNF-alpha, flt-2/flk-3, etc. can be added during the co-culture. For the activation of T cells for tumor therapy it is particularly preferred to use IL-2. For the activation of dendritic cells it is preferred to use GM-CSF, TNF-alpha and IL-4.

In a further preferred embodiment such growth factors or factors which mediate a co-stimulatory signal or an adhesion signal can be bound to streptavidin when the cell surface is biotinylated and thus be bound to the cell surface. This is particularly advantageous when vesicles of tumour cells are used which do not usually carry a co-stimulatory signal. In this case it is particularly preferable to for example bind streptavidin-bound B7 to the cell surface. This can increase the immune reactivity of tumour cells.

The following examples and publications further elucidate the invention the protective scope of which results from the patent claims. The described processes are to be understood as examples which still describe the subject matter of the invention even after modifications.

EXAMPLE 1

Culture of Stroma Cells

The stromal cell lines L87/4 and L88/5 were cultured in long-term medium as described by Thalmeier et al., Blood 83 (1994) 1799–1807 and WO 95/02040. The stromal cell lines L87/4 and L88/5 were cultured as one layer cultures in plastic culture flasks (NUNC, Wiesbaden-Biebrich) using LTC medium containing $10^{-6}$ M hydrocortisone (HSS). The cells were incubated at 37° C. in a $CO_2$ incubator (air/5% $CO_2$), trypsinized and subcultured at an initial concentration of $3 \times 10^5$ cells/25 $cm^2$ culture flask.

Long-term Medium:
  McCoy's 5a containing 12.5% FCS; 12.5% HS; 1% sodium bicarbonate; 1% sodium pyruvate; 1% vitamins; 0.4% non-essential amino acids; 0.8% essential amino acids; 200 mM L-glutamine; 1% penicillin/streptomycin; $10^{-4}$ M α-thioglycerol; $10^{-6}$ M hydrocortisone.

EXAMPLE 2

Isolation of the Stroma Cell Suspension

After reaching confluence the cells are detached with 0.25% trypsin (Gibco) (10 min; 37° C.), the cell count is determined and they are washed in PBS (without $Mg^{2+}$ and $Ca^{2+}$) (10 min; 1200 rpm; RT). The cell pellets (ca. $2-3 \times 10^7$ cells in the case of L87/4; ca. $5 \times 10^7$ cells in the case of L88/5) are resuspended in 1 ml PBS each time.

EXAMPLE 3

Biotinylation of the Stromal Cells

In order to label the cell membranes with biotin, 10 µl biotin-7-NHS solution (D-biotinoyl-ε-aminocaproic acid-N-hydroxysuccinimide ester; Boehringer) is added each time and shaken for 10 min at RT. Free amino groups of the proteins located at or on the cell membrane react with biotin-7-NHS with formation of a stable amide bond. Non-reacted biotin-7-NHS is removed by washing twice with 50 ml PBS each time.

Biotin-7-NHS Solution:
  5 mg biotin-7-NHS in 250 µl DMSO (=20 mg/ml).

EXAMPLE 4

Preparation of Vesicles (modified according to Jett et al., J. Biol. Chem. 252 (1977) 2134–2143)

The biotinylated cells are resuspended in 1 ml aliquots of pre-heated EBSS (Sigma). Subsequently a 90% glycerol solution (37° C.) is added by pipette in 3 equal portions at 5 minute intervals to the cell suspension in order to finally obtain a 30% glycerol solution. All steps are carried out at 37° C. 5 min after the last glycerol addition the cell suspension is cooled for 2 min in an icebath. All further steps are carried out at 4° C. The cells are centrifuged (10 min. 1200 rpm; 4° C.) and the supernatant is discarded. The cells are burst (hypotonic shock) by the rapid addition of 1 ml cold Tris buffer and briefly vortexed. After 5 min incubation in the icebath the lysed cells are centrifuged (10 min; 1000 rpm; 4° C.). The lysate (=supernatant) is filtered with the aid of a 5 µm filter unit (Millex®-SV filter unit; Millipore). The pelleted cell debris is in turn resuspended in 1 ml cold Tris buffer, vortexed and also filtered through a 5 µm filter unit. As a result the larger membrane particles and the cell nuclei are separated and a homogeneous suspension is obtained composed of (<2 µm) membrane vesicles of approximately equal size. The filtrates are combined and centrifuged (20 min; 6700×g; 4° C.).

Glycerol Solution:
  90% w/v Earle's balanced salt solution (EBSS).

Tris Buffer:
  10 mM Tris-Cl, pH 7.4; 1 mM $MgCl_2$; 1 mM $CaCl_2$.

EXAMPLE 5

Immobilization of Membrane Vesicles by Means of a Biotin-streptavidin Binding The pelleted membrane vesicles are taken up in ca. 5 ml medium and plated out in an amount of 50 µl/well in streptavidin-coated 96-well plates. After an incubation period of 5–10 hours at 37° C. in a $CO_2$ incubator (air/5% $CO_2$) the non-bound vesicles can be removed by washing.

Plate Technology:
  The cell culture plates (sterile) coated with streptavidin can be very homogeneously coated with the biotinylated membrane vesicles (<2 µm) i.e. with very small and relatively uniform spaces between them. The vesicles adhere to the plates via the biotin-streptavidin binding after 5–10 hours incubation period and remain as a uniform coating even after vigorous shaking or rinsing (FIG. 1).

The coating of the plates results in a homogeneous vesicle lawn which could be stored for at least one week.

Figure 2:
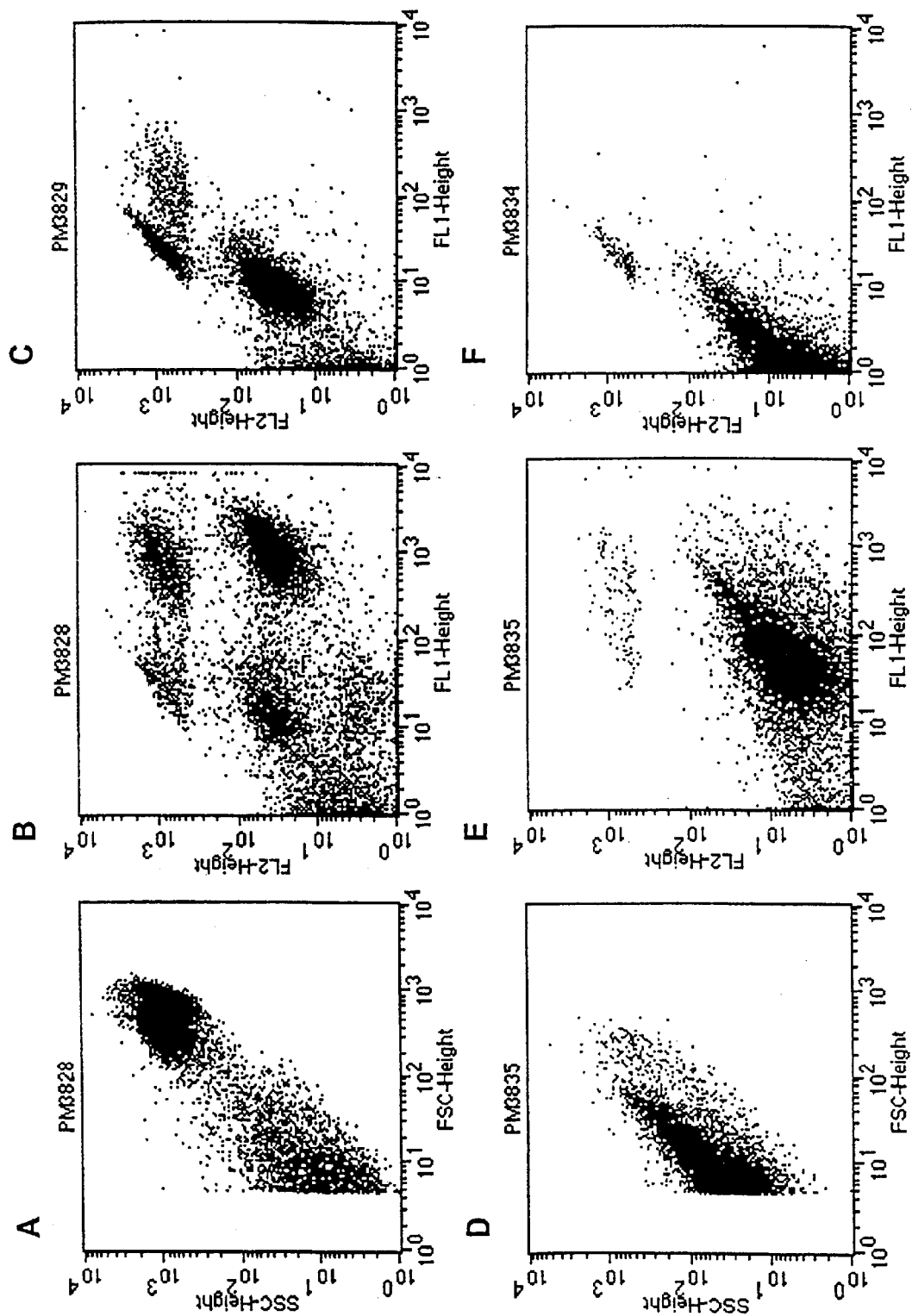
FIG. 2 shows the flow-cytometric analysis of cells and isolated vesicles

Analysis of the Vesicles:
  In order to examine whether the prepared vesicles were also actually labelled with biotin and how uniformally this labelling occurred, the cells and vesicles were analysed at various times during the preparation. FIG. 2B clearly shows that the majority of the cells are biotinylated (right lower cluster) after labelling with FITC-conjugated streptavidin. The control preparation of non-biotinylated cells is shown in FIG. 2C. The prepared vesicles (FIG. 2E) are all biotinylated. The control preparation of non-biotinylated vesicles is shown in FIG. 2F.

Even after an incubation period of at least one week at 37° C., the individual vesicles were still clearly recognizable in the streptavidin plates and still bound to the plates. Equally the vesicles could be stored for a period of at least 8 days at 4° C. in medium or buffer without reducing their ability to attach via the biotin-streptavidin binding. The vesicles could be used in a comparable manner to freshly prepared vesicles after brief vortexing.

EXAMPLE 6

Co-culture of Human CD34+ Cells from Umbilical Cord Venous Blood or Bone Marrow on Vesicle-coated 96-well Plates Compared to Irradiated Cell Layers or Plastic Isolation of CD34+ Cells:
  The method used here is the immunomagnetic separation of CD34+ cells from mononuclear cells (MNC) with the aid of Dynabeads® (Deutsche Dynal GmbH, Hamburg). For this the precursor cells were labelled with paramagnetic beads covalently bound to CD34 antibodies, separated from the unlabelled cells in a magnetic field and subsequently the beads were detached from the cells with the aid of a specific antibody preparation (DETACHaBEAD®, Deutsche Dynal GmbH). Umbilical cord venous blood was diluted 1:5 with RPMI (containing 25 units/ml heparin and 10 µg/ml DNase) in order to ensure the most efficient possible yield of MNC. The cell suspension was layered on Ficoll-Paque® and centrifuged for 30 min at RT and 1600 rpm. Subsequently the cells at the interphase were washed twice (RPMI/heparin/DNase), the cells were taken up in RPMI/10% FCS+DNase and the cell count was determined. The M-450 CD34 beads were washed with RPMI/10% FCS before use and well-mixed with the cells in Eppendorf vessels. The optimal ratio of beads to cells was 1:1. The cell bead mixture was incubated for 45 min at 4° C. while gently rotating. Subsequently the labelled cells were separated with the aid of a Dynal MPC magnet by washing four times and taken up in 100 µl RPMI/10% FCS.

In order to detach the beads from the cells, the cell suspension was well-mixed with one unit (10 µl) DETACHaBEAD® per $10^7$ Dynabeads and incubated for 60 min at RT while gently rotating. The detached CD34+ cells were separated from the beads with the aid of a magnet by washing twice. Subsequently the cell count was determined and the precursor cells were subjected to the various tests.

DNase Solution:
dissolve 10 mg DNAase in 1 ml PBS; filter sterile

Two Step Cultures:
The stromal cell lines were sown at a cell density of $10^4$/well in LTC medium containing $10^{-6}$M HSS in 96-well plates, incubated for 24 hours at 37° C. in an incubator, irradiated with 15 or 20 gray (caesium 137, gamma cell irradiation apparatus) and cultured for a further 12–24 hours. Then the CD34+ precursor cells isolated from umbilical cord venous blood (3.2.10.1 or 3.2.10.2) were sown on the various cell layers (1–2×$10^3$ CD34+ cells/well) or on immobilized vesicles. Half of the consumed medium was removed once per week and replaced by fresh medium. After the end of the culture period (in this case 2 weeks) all cells were harvested, the cell count was determined and they were used in methylcellulose cultures.

Methylcellulose Culture:
In order to quantify the clonality of CD34+ cells which had been cultured in various vesicle-coated 96-well plates or on various stromal layers, methylcellulose cultures were prepared. For this semisolid cultures were set up containing $10^4$ to 2×$10^4$ non-adherent cells per ml in 14% IMDM, 30% FCS, 1% BSA, 5% PHA-LCM, $10^{-4}$ M each of L-glutamine and α-thioglycerol, 0.98% methylcellulose, 3 units/ml EPO and 100 ng/ml KL. These cultures were incubated at 37° C. in 1 ml volume in 35 mm tissue culture plates (air/5% $CO_2$) and the colonies were counted after 14 days with the aid of an invert microscope (Zeiss), Results of Clonal Growth:
The number of GM-CFC in the co-culture on L87/4 or L88/5 was 465.5 or 116.3 clones. In the co-culture on corresponding vesicles 90 and 76.3 GM-CFC clones respectively grew. The number of BFU-E in the co-culture of L87/4 or L88/5 was 104.5 or 13.8 clones respectively. In the co-culture on respective vesicles 27.5 or 52.5 BFU clones respectively grew. The co-culture of CD34 cells on vesicles of the stroma cell line L87/4 compared to the plastic surface alone of cell culture vessels resulted in 21.3 GM-CFC and 640 BFU-E clones in the vesicle co-culture and 16.3 GM-CFC and 217.5 BFU-E clones in the culture on a plastic surface.

List of References

Bayer, E. A., Wilchek, M., Liposome Technology, CRC Press, Inc. 1984, Vol. III, 127–135
Bergers, J. J., et al., Cancer Immunol. Immunother. 34 (1992) 233–240
Bergers, J. J., et al., Journal of Controlled Release 29 (1994) 317–327
Bloemen, P. G. M., et al., FEBS Letters 357 (1995) 140–144
Brown, P. M., Silvius, J. R., Biochimica et Biophysica Acta 1023 (1990) 341–351
Chen, B., et al., Cell Immunol. 118 (1989) 458–469
Clark, E. A., Ledbetter, J. A., Nature 367 (1994) 425–428
Corley, O., Loughrey, H. C. Biochimica et Biophysica Acta 1195 (1994) 149–156
Dou, Y. M., et al., Thymus 23 (1994) 195
Einerhand, M. P. W., et al., Blood 81 (1993) 254
EP-A 0 701 130
Fossati, G. et al., International Journal of Cancer, 42 (1988) 239–245
Geppert, T. D., Lipsky, P. E., The Journal of Immunology 6, Vol. 138 (1987) 1660–1666
Gregoriadis, G., Immunology Today, Vol. 11, No. 3 (1990) 89–97
Herold, C., et al., MS-Medecine Sciences, Vol. 11, No. 5 (1995) 669–680
Herrmann, S. H., Mescher, M. F., Proc. Natl. Acad. Sci. USA, Vol. 78, No. 4 (1981) 2488–2492
Jahn, S., et al., Allerg. Immunol. 33 (1987) 239–244
Jett et al., J. Biol. Chem. 252 (1977) 2134–2143
June, C. H., et al., Immunology Today 15 (1994) 321
Koller, M. R., et al., Biotechnology 11 (1993) 358
Loughrey, H. C. et al., FEBS 13102, Vol. 332, No. 1,2 (1993) 183–188
Mayordomo, J. I., et al., Nature Medicine, Vol. 1, No. 12 (1995) 1297–1302
Mescher, M. F., Immunological Reviews 146 (1995) 177
Moy, V. T., Brian, A. A., J. Exp. Med. 175 (1992) 1–7
Nolta, J. A., et al., J. Clin. Invest. 90 (1992) 342
Papahadjopoulos, D., Gabizon, A., Annals of the New York Academy of Sciences, Vol. 507, R. L. Juliane (ed.), 1987, 64–74
Phillips, N. C., et al., Liposomes in the Therapy of Infectious Diseases and Cancer, 1989, Alan R. Liss, Inc. (ed.), p. 15–24
Rosenberg, Immunology Today 9 (1988) 58–62
Sutherland, H. J., Eaves, C. J., Culture of Hematopoietic Cells, Freshney, R. J., et al., (eds.), Wiley Liss, N.Y., 1994, pp. 139
Thalmeier et al., Blood 83 (1994) 1799–1807
Thiele, D., et al., Immunology Today 10 (1989) 375–381
Toksoz, D., et al., Proc. Natl. Acad. Sci. USA 89 (1992)
Walden, P., et al., Nature, Vol. 315 (1985) 327–329
Watts, T. H., et al., Proc. Natl. Acad. Sci. USA, Vol. 81 (1984) 7564–7568
WO 94/23014
WO 95/02040

What is claimed is:

1. A membrane vesicle bound to a binding partner of a biological binding pair, wherein said membrane vesicle contains part of the natural membrane surface of a mammalian cell which includes signal triggering surface proteins;
    wherein said binding partner is capable of binding to another member of the binding pair to immobilize the membrane vesicle on a solid carrier.

2. A solid surface for culturing mammalian cells which require contact with cell surface proteins, comprising a membrane vesicle of a mammalian cell, immobilized on a solid surface, wherein said membrane vesicle contains part of the natural membrane surface of the mammalian cell which includes signal triggering surface proteins;

wherein said membrane vesicle is modified with a first partner of biological binding pair and is immobilized on said solid surface via a second partner of the biological binding pair.

3. The solid surface according to claim 2, further comprising substances which are required for the activation, proliferation or differentiation of cells, bound to said membrane vesicles.

4. A solid surface for culturing mammalian cells which require contact with cell surface proteins, comprising a mixture of membrane vesicles from at least two mammalian cell populations, immobilized on a solid surface, wherein said membrane vesicles contain parts of the natural membrane surface of the mammalian cell populations which include signal triggering surface proteins;

wherein said membrane vesicles are modified with a first partner of a biological binding pair and are immobilized on said solid surface via a second partner of the biological binding pair.

5. A process for culturing a mammalian cell comprising the steps of contacting a first mammalian cell with either a) an immobilized second mammalian cell or b) an immobilized membrane vesicle of a second mammalian cell, wherein said immobilized membrane vesicle contains part of the natural membrane surface of the second mammalian cell which includes signal triggering surface proteins, and culturing said first mammalian cell in the presence of said immobilized second mammalian cell or said immobilized membrane vesicle;

wherein said second mammalian cell or said membrane vesicle is modified with a first partner of a biological binding pair and is immobilized on a solid carrier via a second partner of the biological binding pair.

6. The process according to claim 5, wherein the membrane vesicle is immobilized via a binding partner for a cell surface molecule.

7. The process according to claim 6, wherein the cell surface molecule is selected from the group consisting of a CD molecule, a MHC class I molecule, a MHC class II molecule and mixtures thereof.

8. The process according to claim 5, wherein the second mammalian cell or the membrane vesicle is biotinylated and is immobilized on the solid carrier via streptavidin or avidin.

9. The process according to claim 5, wherein said signal-triggering surface protein is selected from the group consisting of a co-stimulatory signal protein, an antigen presenting receptor, and an adhesion molecule.

10. The process according to claim 9, wherein said co-stimulatory signal protein is from the B7 family or CD40.

11. The process according to claim 9, wherein said antigen presenting receptor is MHC I, MHC II or both MHC I and II.

12. The process according to claim 5, further comprising binding a substance which causes the activation, proliferation and/or differentiation of cells, to said second mammalian cell or membrane vesicle, wherein said substance is bound to the mammalian cell or the mammalian vesicle using a biological binding pair.

13. The process according to claim 8, wherein said membrane vesicle is biotinylated by biotinylating whole cells and subsequently isolating biotinylated membrane vesicles which are formed from said whole cells.

14. The process according to claim 5, wherein said second mammalian cell is a tumor cell.

15. The process according to claim 5, wherein said membrane vesicle is smaller than 4 µm in diameter.

16. The method according to claim 15, wherein said membrane vesicle is smaller than 500 nm in diameter.

17. The process according to claim 5, further comprising adding a growth factor selected from the group consisting of SCF, IL-1, IL-2 IL-3, IL-4 IL-6, IL-11, EPO, G-CSF, GM-CSF, TNF-alpha, flt-2 and flk-3, during culturing.

18. The process according to claim 15, wherein said first mammalian cell is cultured in the presence of a first immobilized membrane vesicle and subsequently cultured in the presence of a second immobilized membrane vesicle.

19. A process for culturing a mammalian cell comprising the steps of contacting a first mammalian cell with immobilized membrane vesicles from at least two mammalian cell populations, wherein said immobilized membrane vesicles contain parts of the natural membrane surface of said mammalian cell populations which include signal triggering surface proteins, and culturing said first mammalian cell in the presence of said immobilized membrane vesicles;

wherein said membrane vesicles are modified with a first partner of a biological binding pair and are immobilized on a solid carrier via a second partner of the biological binding pair.

* * * * *